US00PP22724P2

(12) United States Plant Patent
Barends

(10) Patent No.: US PP22,724 P2
(45) Date of Patent: May 8, 2012

(54) *PELARGONIUM* PLANT NAMED 'FIPELDANCAN'

(50) Latin Name: *Pelargonium peltatum*
Varietal Denomination: Fipeldancan

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/925,601

(22) Filed: Oct. 25, 2010

(51) Int. Cl.
*A01H 5/00* (2006.01)

(52) U.S. Cl. ..... Plt./332

(58) Field of Classification Search ..... Plt./324, Plt./332
See application file for complete search history.

*Primary Examiner* — Susan McCormick Ewoldt
(74) *Attorney, Agent, or Firm* — C. A. Whealy

(57) ABSTRACT

A new and distinct cultivar of *Pelargonium* plant named 'Fipeldancan', characterized by its upright to outwardly spreading plant habit; freely basal branching habit; early and freely flowering habit; double red purple-colored flowers; and good garden performance.

1 Drawing Sheet

Botanical designation: *Pelargonium peltatum.*
Cultivar denomination: 'FIPELDANCAN'.

BACKGROUND OF THE INVENTION

The present invention relates to a new and distinct cultivar of *Pelargonium* plant, botanically known as *Pelargonium peltatum*, commercially referred to as Ivy Geranium, and hereinafter referred to by the name 'Fipeldancan'.

The new *Pelargonium* plant is a product of a planned breeding program conducted by the Inventor in De Lier, The Netherlands. The objective of the breeding program is to create new freely-branching and freely-flowering *Pelargonium* plants with large flowers and attractive leaf and flower coloration.

The new *Pelargonium* plant originated from a cross-pollination made by the Inventor in September, 2005 in De Lier, The Netherlands of a proprietary selection of *Pelargonium peltatum* identified as code number 03-241-02, not patented, as the female, or seed, parent with a proprietary selection of *Pelargonium peltatum* identified as code number 2044, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands in March, 2006.

Asexual reproduction of the new *Pelargonium* plant by vegetative terminal cuttings in a controlled greenhouse environment in De Lier, The Netherlands since July, 2006, has shown that the unique features of this new *Pelargonium* plant are stable and reproduced true to type in successive generations.

SUMMARY OF THE INVENTION

Plants of the new *Pelargonium* have not been observed under all possible environmental conditions. The phenotype may vary somewhat with variations in environment such as temperature and light intensity without, however, any variance in genotype.

The following traits have been repeatedly observed and are determined to be the unique characteristics of 'Fipeldancan'. These characteristics in combination distinguish 'Fipeldancan' as a new and distinct cultivar of *Pelargonium* plant:

1. Upright to outwardly spreading plant habit.
2. Freely basal branching habit.
3. Early and freely flowering habit.
4. Double red purple-colored flowers.
5. Good garden performance.

Plants of the new *Pelargonium* differ primarily from plants of the parent selections in growth habit and plant habit as plants of the new *Pelargonium* are more vigorous in growth habit and more uniform in plant habit than plants of the parent selections.

Plants of the new *Pelargonium* can be compared to plants of *Pelargonium peltatum* 'Fislina', disclosed in U.S. Plant Pat. No. 16,681. In side-by-side comparisons conducted in De Lier, The Netherlands, plants of the new *Pelargonium* differed from plants of 'Fislina' in the following characteristics:

1. Plants of the new *Pelargonium* were more freely branching than plants of 'Fislina'.
2. Leaves of plants of the new *Pelargonium* had a more pronounced zonation pattern than leaves of plants of 'Fislina'.
3. Plants of the new *Pelargonium* had darker-colored flowers than plants of 'Fislina'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant.

The photograph comprises a side perspective view of a typical flowering plant of 'Fipeldancan' grown in a container.

DETAILED BOTANICAL DESCRIPTION

The aforementioned photograph and following observations, measurements and values describe plants grown during the spring in 12-cm containers in a glass-covered greenhouse in De Lier, The Netherlands and under conditions which closely approximate commercial *Pelargonium* production. During the production of the plants day temperatures ranged from 17° C. to 18° C. and night temperatures ranged from 14° C. to 16° C. Plants were twelve weeks old when the photograph and the description were taken. In the detailed description, color references are made to The Royal Horticultural Society Colour Chart, 2007 Edition, except where general terms of ordinary dictionary significance are used.

Botanical classification: *Pelargonium peltatum* 'Fipeldancan'.

Parentage:

*Female, or seed, parent*.—Proprietary selection of *Pelargonium peltatum* identified as code number 03-241-02, not patented.

*Male or pollen parent*.—Proprietary selection of *Pelargonium peltatum* identified as code number 2044, not patented.

Propagation:

*Type*.—By vegetative terminal cuttings.

*Time to initiate roots, summer*.—About four days at temperatures of 22° C.

*Time to initiate roots, winter*.—About one week at temperatures of 22° C.

*Time to produce a rooted young plant, summer*.—About 16 days at temperatures of 22° C. to 30° C.

*Time to produce a rooted young plant, winter*.—About three weeks at temperatures of 20° C. to 25° C.

*Root description*.—Medium in thickness, fibrous; whitish grey in color.

*Rooting habit*.—Moderate branching, medium density.

Plant description:

*Plant habit*.—Upright to outwardly spreading and eventually trailing plant habit; uniformly mounded; densely foliated.

*Growth and branching habit*.—Moderately vigorous growth habit; freely basal branching habit with about four to six lateral branches per plant.

*Plant height, to top of umbels*.—About 20 cm to 22 cm.

*Plant height, to top of leaves*.—About 10 cm to 12 cm.

*Plant width*.—About 40 cm to 45 cm.

*Lateral branches*.—Length: About 10 cm to 15 cm. Diameter: About 3 mm to 5 mm. Internode length: About 1 cm to 2 cm. Texture: Pubescent. Strength: Moderately strong. Color: Close to 144A.

Foliage description:

*Arrangement*.—Alternate; simple.

*Length*.—About 6 cm to 7 cm.

*Width*.—About 7 cm to 8 cm.

*Shape*.—Roughly orbicular; palmately lobed.

*Apex*.—Acute.

*Base*.—Cordate; open.

*Margin*.—Entire; palmately lobed.

*Venation pattern*.—Palmate.

*Texture, upper surface*.—Smooth, glabrous.

*Texture, lower surface*.—Slightly pubescent.

*Color*.—Developing and fully expanded leaves, upper surface: Close to N137A; venation, close to N137A. Developing and fully expanded leaves, lower surface: Close to N146A; venation, close to 146A. Zonation pattern, upper surface only: Location: Center of leaf. Width: About 1.5 cm. Color: Close to 147A. Petiole: Length: About 2.5 cm to 7.5 cm. Diameter: About 2 mm. Texture, upper and lower surfaces: Smooth, glabrous. Color, upper surface: Close to 146A. Color, lower surface: Close to 146B.

Flower description:

*Flower arrangement*.—Double flowers arranged in rounded hemispherical umbels arising from apical leaf axils; umbels displayed above the foliage on strong peduncles; flowers face upright to outwardly.

*Fragrance*.—None detected.

*Quantity of flowers*.—Freely flowering habit; about 15 to 29 flowers and flower buds per umbel; about 15 to 18 umbels develop per plant.

*Flowering season*.—In The Netherlands, flowering is continuous from spring until frost in the autumn; early flowering habit, plants begin flowering about six to eight weeks after planting.

*Flower longevity*.—Individual flowers last about 2 to 14 days on the plant; flowers persistent.

*Umbel height*.—About 4.5 cm to 5 cm.

*Umbel diameter*.—About 8 cm to 9 cm.

*Flower diameter*.—About 5 cm.

*Flower depth* (*height*).—About 1.5 cm.

*Flower buds*.—Length: About 1.3 cm. Diameter: About 7 mm. Shape: Broadly elliptic. Color: Close to 146C tinged with close to 51A.

*Petals*.—Quantity per flower: About ten to twelve. Length: About 2.5 cm to 2.7 cm. Width: About 1.5 cm to 1.7 cm. Shape: Spatulate to obovate. Apex: Obtuse. Base: Attenuate. Margin: Entire. Texture, upper and lower surfaces: Smooth, glabrous; satiny. Color: When opening, upper surface: Close to N57A. When opening, lower surface: Close to 50B. Fully opened, upper surface: Close to 58B; color becoming closer to N57D with development. Fully opened, lower surface: Close to 52C; color becoming closer to 56A with development.

*Petaloids*.—Quantity per flower: If present, one or two. Length: About 1 cm to 1.5 cm. Width: About 1 cm to 1.5 mm. Shape: Irregularly oblanceolate. Apex: Obtuse. Base: Attenuate. Margin: Entire. Texture, upper and lower surfaces: Smooth, glabrous; satiny. Color: When opening and fully opened, upper surface: White tinged with close to N57A. When opening and fully opened, lower surface: Close to 56A.

*Sepals*.—Quantity per flower/arrangement: Five in a single whorl. Length: About 1 cm. Width: About 4 mm. Shape: Lanceolate. Apex: Acute. Base: Cuneate. Margin: Entire. Texture, upper surface: Pubescent. Texture, lower surface: Smooth, glabrous. Color, upper and lower surfaces: Close to 146C to 146D.

*Peduncle* (*umbel stem*).—Length: About 10 cm to 17 cm. Diameter: About 3 mm to 4 mm. Strength: Strong. Angle: Erect to about 30° C. from vertical. Texture: Pubescent. Color: Close to 146A.

*Pedicel* (*individual flower stem*).—Length: About 2.5 cm to 2.7 cm. Diameter: About 2 mm. Strength: Moderately strong. Angle: Erect to about 60° C. from vertical. Texture: Pubescent. Color: Close to 146A tinged with close to 187A.

*Reproductive organs*.—Androecium: Stamen quantity per flower: If present, up to eight. Filament length: About 7 mm. Filament color:. Close to 155A. Anther length: About 2 mm. Anther shape: Oblong. Anther color: Close to 47A. Pollen amount: Moderate. Pollen color: Close to 172C. Gynoecium: Pistil quantity per flower: One. Pistil length: About 1 cm to 1.5 cm.

Stigma shape: Tapering; reflexed. Stigma color: Close to 64A. Style length: About 3 mm. Style color: Close to 64A. Ovary color: Close to 64A.

*Fruits/seeds*.—Fruit and seed development have not been observed.

Disease/pest resistance: Plants of the new *Pelargonium* have not been observed to be resistant to pathogens and pests common to *Pelargoniums*.

Garden performance: Plants of the new *Pelargonium* have been observed to tolerate rain, wind and temperatures ranging from about 0° C. to about 40° C. and have demonstrated good garden performance.

It is claimed:

1. A new and distinct *Pelargonium* plant named 'Fipeldancan' as illustrated and described.

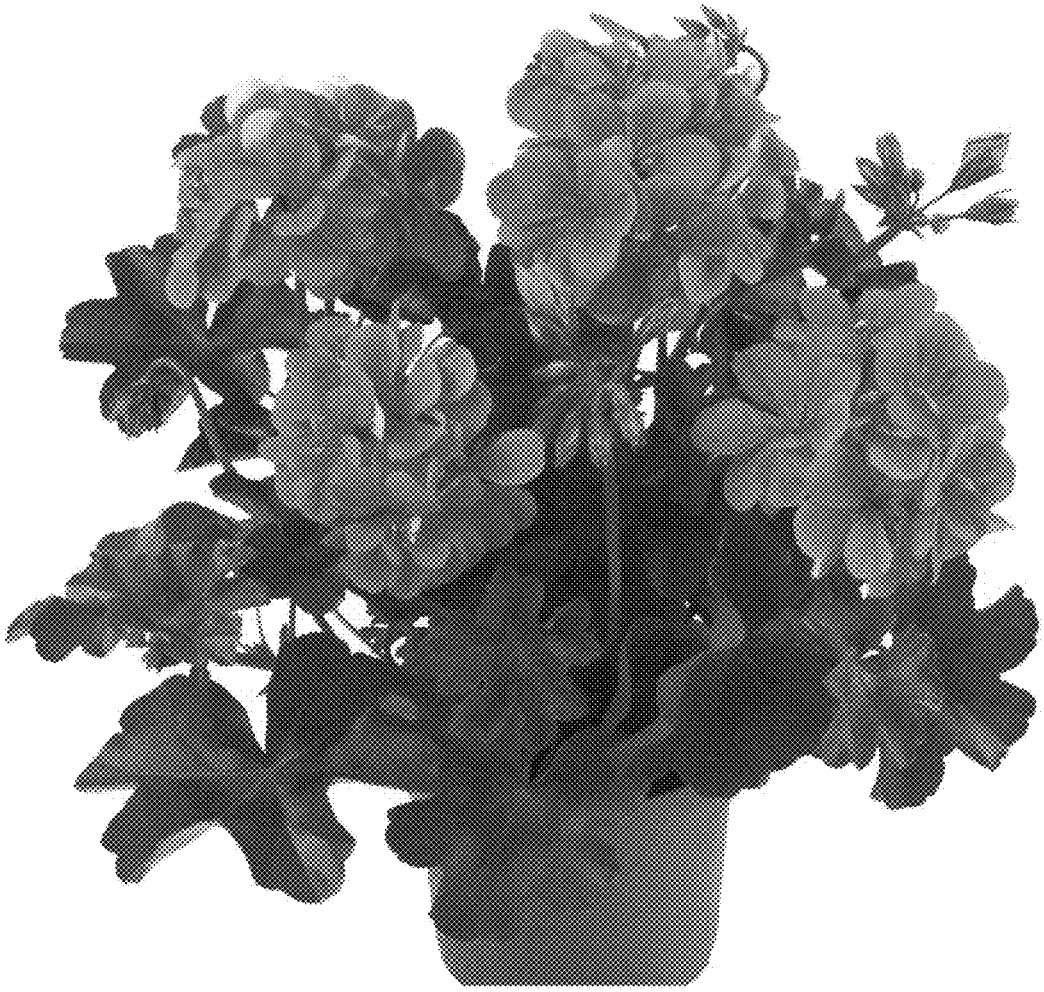

* * * * *